United States Patent [19]
Lilitkarntakul et al.

[11] Patent Number: 5,344,968
[45] Date of Patent: Sep. 6, 1994

[54] METHOD FOR PRODUCING O-ALKOXYBENZOIC ACID

[75] Inventors: Suchart Lilitkarntakul; Shukichi Nabekawa; Masao Takada, all of Tokyo; Katsuyuki Ogura, Narashino, all of Japan

[73] Assignee: Nippon Chemical Industrial Co., Ltd., Tokyo, Japan

[21] Appl. No.: 902,820

[22] Filed: Jun. 23, 1992

[30] Foreign Application Priority Data

Jun. 27, 1991 [JP] Japan .................................. 3-185476
Apr. 10, 1992 [JP] Japan .................................. 4-118163

[51] Int. Cl.$^5$ ............................................. C07C 65/00
[52] U.S. Cl. .................................... 562/474; 562/473
[58] Field of Search ................................ 562/474, 473

[56] References Cited

U.S. PATENT DOCUMENTS

4,288,386 9/1981 Soula .................................. 562/474
4,845,276 7/1989 Yu .

FOREIGN PATENT DOCUMENTS

2414498 1/1975 Fed. Rep. of Germany .

*Primary Examiner*—Paul J. Killos
*Attorney, Agent, or Firm*—Oblon, Spivak, McClelland, Maier & Neustadt

[57] ABSTRACT o-Methoxy benzoic acid is produced by reacting chlorobenzoic acids having at least one chlorine atom at least at the ortho position with lower alcohol in the presence of a copper salt and a lower alkyl as a catalyst under moderate reaction conditions. o-Methoxy benzoic acid is useful as an intermediate for pharmaceutical, agricultural chemicals, and the like.

11 Claims, No Drawings

METHOD FOR PRODUCING O-ALKOXYBENZOIC ACID

BACKGROUND OF THE INVENTION

The present invention relates to a method for producing o-alkoxybenzoic acid. More specifically, the present invention relates to a method for producing o-monoalkoxybenzoic acid or o-dialkoxybenzoic acid, being useful as intermediates for pharmaceutical agents, agricultural chemicals, dyes, fragrances and the like and useful as functional pharmaceutical agents such as a second pharmaceutical solution for dental cement, components of adhesive agents and the like.

The following methods have conventionally been known as techniques for producing o-monoalkoxybenzoic acid as an o-alkoxybenzoic acid;

1. A method represented by a reaction formula (1)

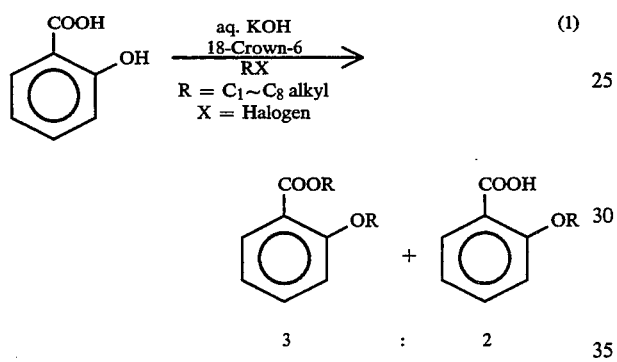

(wherein R represents a methyl-, ethyl-, propyl-, butyl-, n-pentyl-, n-hexyl- or n-octyl group; and X represents bromine, chlorine or iodine), comprising adding alkyl halide to an aqueous potassium hydroxide solution of o-hydroxybenzoic acid with 18-crown-6 added as a catalyst, and reacting them together [Zh. Org. Khim. 23(3), 667–668 (1987)];

2. A method represented by a reaction formula (2)

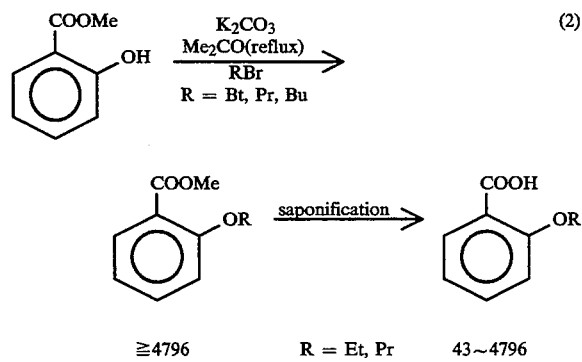

comprising adding alkyl bromide to a potassium carbonate solution of methyl o-hydroxybenzoate and reacting them together under reflux [Azerb. Khim. Zh., (2) 46–49 (1987)];

The following two methods are known as techniques for producing 2,6-dialkoxybenzoic acid;

3. A method represented by a reaction formula (3)

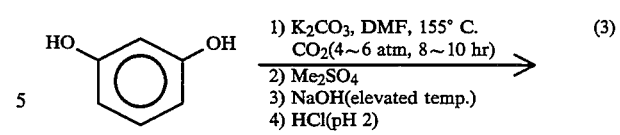

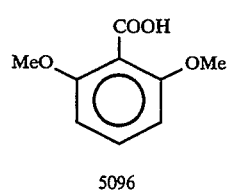

comprising effecting a Kolbe Schmitt reaction using resorcin as a starting material, methylating the reaction product with dimethyl sulfate, and further processing the product in an aqueous dilute sodium hydroxide solution at a higher temperature (Specifications of Hungarian Patent Nos. 162,756 and 162,757).

4. A method represented by a reaction formula (4)

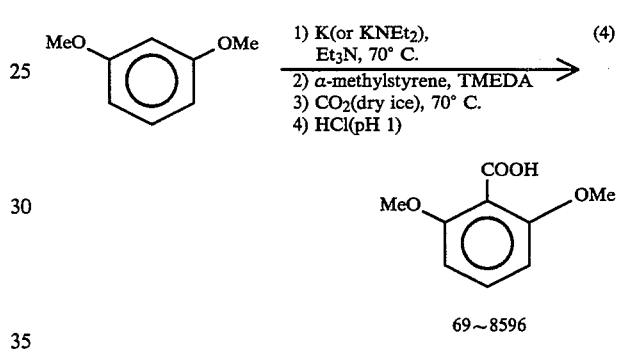

comprising metallation with metal potassium using 1,3-dimethoxybenzene as a starting material, and subsequently making the resulting product coexist with a base such as TMEDA (N,N,N,N-tetramethyl-1,2-ethylene diamine) (Specifications of U.S. Pat. Nos. 4,845,276 and 4,845,277; Japanese Patent Laid-open Nos. 2-108650 and 2-108651).

However, the method described in (1) is industrially disadvantageous in that a mixed product of o-alkoxybenzoic acid alkyl ester and o-alkoxybenzoic acid is obtained at a ratio of 3:2, and additionally in that the 18-crown-6 to be used as a catalyst is extremely expensive. The method described in (2) is not suitable industrially, because costly alkyl bromide must be used for the reaction and o-alkoxybenzoic acid methyl ester must be subjected to another step for hydrolysis.

The method described in (3) cannot be considered advantageous for industrial practice. The method employs potassium salt and carbon dioxide gas and involves a Kolbe Schmitt reaction under high temperature and high pressure conditions. In addition, a side reaction of the positional isomer via resorcin occurs, resulting in an extremely low yield of objective product, 2,6-dimethoxybenzoic acid, so that improvement of increase in yield is difficult. According to the reaction described in (4), a problem concerning selectivity can be avoided and the yield of the objective product gets higher. An Italian publication [Gazzetta Chimica Italiano, 111, 123 (1981)] describes that, if the starting material is a 1,3-dialkylbenzene other than 1,3-dimethoxybenzene, such as 1,3-diisopropylbenzene or 1-propoxy-3-methoxybenzene, the yield and selectivity are both poor because of the positional isomer of by-products, so it is not preferable method for an industrial reaction.

SUMMARY OF THE INVENTION

The present invention is aimed at improving the drawbacks described above, and the objective of the present invention is to provide a general method for producing o-alkoxybenzoic acid in an industrially advantageous manner, employing o-chlorobenzoic acid as the starting material.

In order to achieve the above objective, the method for producing o-alkoxybenzoic acid in accordance with the present invention, comprises reacting a specific o-chlorobenzoic acid with a lower alcohol in the presence of a copper salt and an alkylamine.

The o-chlorobenzoic acid as the starting material of the present invention refers to a benzoic acid having a chlorine atom at least at ortho position, as represented by Chemical Formula (5) or Chemical Formula (6).

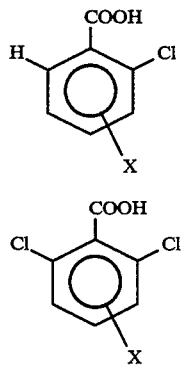

In accordance with the present invention, a lower alcohol cannot attack the halogen atom at the meta- or para position of o-chlorobenzoic acid, but can selectively attack the chlorine at the ortho position. In terms of such relations, the o-chlorobenzoic acid may be one wherein halogen atoms such as chlorine, bromine or iodine or the like may exist at the meta and para positions.

Therefore, as the benzoic acid has one or two chlorine atoms, there may be illustrated, for example, o-chlorobenzoic acid, 2,3-dichlorobenzoic acid, 2,4-dichlorobenzoic acid, 2,5-dichlorobenzoic acid, 2-chloro-3-bromobenzoic acid, 2-chloro-4-bromobenzoic acid, 2-chloro-5-bromobenzoic acid, o-dichlorobenzoic acid, 2,3,6-trichlorobenzoic acid, 2,4,6-trichlorobenzoic acid, 2,6-dichloro-3-bromobenzoic acid and the like.

As the reaction catalyst, copper salts such as cuprous chloride and cupric chloride, or copper sulfate may be used. Cuprous chloride in particular is preferably used. As the co-catalyst, may be used lower alkylamines such as, for example, monomethylamine and dimethylamine, but dimethylamine is preferably used the present invention, and a copper-amine complex prepared by mixing them together may be used, depending on need. For the alcoholysis, an excessive amount of a lower alcohol is used as the solvent and alkoxylating agent.

The lower alcohol includes those with carbon numbers of 1 to 5, for example, methanol, ethanol, propanol, butanol, pentanol, isopropyl alcohol, isobutyl alcohol, sec-butyl alcohol, tert-butyl alcohol, isopentyl alcohol, neopentyl alcohol and the like.

The ratios of the above reagents vary, depending on the reaction conditions and the types of reagents. In many cases, however, the copper salt, a lower alkyl amine and lower alcohol are in the range of 0.1 to 0.5 mol, 1 to 10 mol and 10 to 150 mol, respectively, per 1 mol of o-dichlorobenzoic acid; and preferably, in the range of 0.2 to 0.3 mol, 3.0 to 6.0 mol and 50 to 120 mol, respectively.

When monochlorobenzoic acid is used as a starting material only half the amount of the copper salt and a lower alkylamine normally required is sufficient.

Using the individual reagents of the ratios described above, the method of the present invention progresses according to the following reaction formulae 7 and 8.

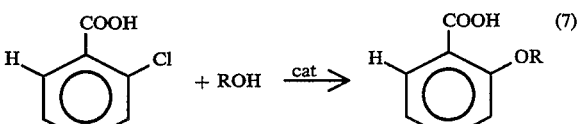

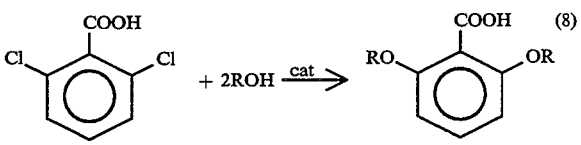

These reactions are effected in an inert-gas (N$_2$) atmosphere under agitation for 1 to 50 hours, preferably 7 to 15 hours, but the reactions do not progress at ambient temperature. Thus, the reactions are effected at 50° to 100° C., preferably at 80° to 90° C. After the completion of the reactions, the reaction product is dissolved in water after removal of the solvent (lower alcohol) and separation of water-insoluble part. Water-soluble part is then crystallized in an acidic liquid of around pH 2, or is purified by chromatography on a silica gel column, thus, recovering the product.

According to the present invention, an o-mono- or o-dialkoxybenzoic acid can be produced at a yield of 60 to 95% and a purity of 90% or more.

The present invention will now be explained as follows.

EXAMPLE 1

Synthesis of o-methoxybenzoic acid from o-chlorobenzoic acid

In a 200-ml three-neck flask equipped with a cooling column and a thermometer were charged and dissolved 2.3 g of o-chlorobenzoic acid (14.6 mM), 0.38 g of cuprous chloride (3.8 mM) in 50 ml of methanol. After 50 ml of a methanol solution containing 20% dimethylamine (about 39 g) was added and the inside of the reaction system was substituted with N$_2$ atmosphere, heating under agitation (in a bath temperature of 80° C. and at a system temperature of 65° C.) of the resulting mixture solution was initiated, and the color of the solution then developed into a bluish green. The reaction mixture solution was sampled periodically over time, and were diluted with the same volume as the sample of the medium for reversed-phase high-performance chromatography (reversed-phase HPLC) was diluted, to follow the progress of the reaction.

The conditions of the reversed-phase HPLC followed the prescription hereinbelow:

1. Column: Pack C18 Shiseido, 46 mm $\phi \times$ 150 mm;
2. Medium (buffer solution): In 1,650 ml of water was dissolved 60.3 g of Na$_2$HPO$_4$.12H$_2$O (pH 9.2), followed by addition of 24 ml of $H_3PO_4$ for the adjustment of the solution to pH 2.1.

To the resulting solution was added the same volume of water with methanol and then to passing the mixture solution through a membrane filter (of a pore size of 0.5 μm, manufactured by Advantec Toyo) in order to degas the medium. The resulting filtrate was designated as the medium.

Although the product was analyzed over time, after one hour, a single peak was obtained (at a complete conversion rate), whereby the completion of the reaction was confirmed. Subsequently, the methanol medium was removed through an aspirator at 40°–50° C. and 140 mmHg for 1.5 hours, to obtain a blue mixture solution. This solution was dissolved in 50 ml of pure water, heated to about 80° C., and filtrated out water-insoluble part, followed by dropwise addition of 1.2 ml of conc. HCl (pH 1~2) to the resulting filtrate, resulting in a uniform mixture solution of green. Cooling was continued to deposit plate-like crystal. The solid crystal was filtered prior to washing with an aqueous hydrochloric acid (0.25N), followed by drying at 80° C. for two hours, to obtain about 1.8 g of a crystalline product. Structure analysis of the product by 60 MHz $^1H$ NMR, IR(KBr), GC-MS(E1, CI) was carried out. It was confirmed that the product was o-methoxybenzoic acid (m.p. of 99° to 100° C.), at a yield of 81.1% and a purity of 90.5% compared with the standard (Aldrich).

Instead of cuprous chloride, either cupric chloride or copper sulfate was used as the catalyst, but no substantial change was observed in the reaction rate and yield (purity).

EXAMPLE 2

Synthesis of 4-chloro-2-methoxybenzoic acid from 2,4-dichlorobenzoic acid

Except for using 2.8 g of 2,4-dichlorobenzoic acid (14.6 mM), 0.75 g of cuprous chloride (7.5 mM) and 100 ml of methanol containing 20% dimethylamine (77 g), the same apparatus, reagents and procedures were employed for reaction as in Example 1. The reaction was followed by reversed-phase HPLC as in Example 1, and as a result, completion of the methanol reaction within two hours was confirmed. After the methanol was removed, 50 ml of water was added and heated in a bath temperature of 80° C., to turn the solution into a uniform mixture solution of green. The green solution was cooled in ice-water to a room temperature. Then, 1.2 ml of conc. HCl was added to consequently deposit needle-liuke crystal. Effecting separation, washing and drying processes in the same manner as in Example 1, about 2.3 g of 4-chloro-2-methoxybenzoic acid was obtained in crystal at a yield of 86.3%. Concerning $^1H$-NMR, IR(KBr), GC-MS$_{E1}$ and melting point, the product was confirmed to show the data agreeable with the reference standard data.

EXAMPLE 3

Synthesis of 2,6-dimethoxybenzoic acid from 2,6-dichlorobenzoic acid

Except for using 2.8 g of 2,6-dichlorobenzoic acid (14.6 mM) as the starting material, the same apparatus, reagents and procedures were employed for the reaction as in Example 2. The reaction was followed by reversed-phase HPLC as in Example 1, and as a result, completion of the reaction was confirmed within 7~10 hours. After the methanol was removed, 50 ml of water was added and heated in a bath temperature of 80° C., to turn the solution into a uniform mixture solution of green. The green solution was cooled in ice-water to a room temperature. Then, 1.2 ml of conc. HCl was added to consequently deposit needle-like crystals. Subsequently effecting separation, washing and drying processes in the same manner as in Example 1, about 2.2 g of crystal was obtained. The structure analysis of the product was done by using $^1H$-NMR, IR(KBr), and GC-MS(E1, CI). It was confirmed that the product was 2,6-dimethoxybenzoic acid (mp of 188°–189° C.). The yield was 82.4%, and the purity was 97.2% compared with the standard (Aldrich). Even when the above reaction was effected in a pressure-resistant sealed vessel and the volume of the 20% dimethylamine solution in methanol was reduced to 50 ml (about 38 g), there could not be observed any influence in the yield. Therefore, it was determined that the following examples were to be effected in a pressure-resistant sealed vessel.

EXAMPLE 4

Synthesis of o-ethoxybenzoic acid from o-chlorobenzoic acid

In a pressure-resistant sealed vessel were dissolved 1.14 g of o-chlorobenzoic acid (7.3 mM) and 0.18 g of copper (I) chloride (1.8 mM) in 6.5 ml of an ethanol solution containing 20% dimethylamine (about 5 g) prior to additionof ethanol to a total volume of 50 ml. The reaction system was substituted with an $N_2$ atmosphere, and a manometer was mounted on the vessel prior to sealing, followed by heating at 100° C. After the heating, the pressure inside the system was 1.5–2.0 kgf/cm$^2$. The reaction mixture solution was sampled periodically over time, to follow the progress of the reaction by gas chromatography-mass spectrum (GC-MS$_{g1}$).

The GC-MS conditions followed the prescription hereinbelow:
1. Column: capillary, 30 m×0.25 μm, DB-1 (non-polar);
2. Column temperature: starting at 100° C., temperature increase of 10° C./min for 15 minutes.

Fifteen hours later, the o-chlorobenzoic acid was completely eliminated, and the reaction was terminated. Then, the ethanol solvent was removed through an aspirator (80° C., 200 mmHg for one hour), to obtain a residue of 4.4 g. This residue was isolated and purified by column chromatography in a column packed with 200 g of silica gel (Wakogel, C300, manufactured by Wako Chemicals, Co. Ltd.), using n-hexane and ethyl acetate of a ratio of 2:1, to produce 1.0 g of an oily o-ethoxybenzoic acid (yield of 82.5%). Compared with the standard (Aldrich), the confirmation of the product was done using $^1H$-NMR, IR(neat), and GC-MS$_{E1}$. By $^1H$-NMR, IR(KBr), GC-MS$_{E1}$ and melting point (mp 122° C.), benzoic acid (11%) was confirmed as an impurity. The same method was effected, except that the volume of the dimethylamine as the starting material was doubled. The result showed that the reaction was shortened to about 5 hours to obtain 1.1 g of o-ethoxybenzoic acid (yield of 91.0%).

EXAMPLE 5

Synthesis of 2,6-diethoxybenzoic acid from 2,6-dichlorobenzoic acid

In a pressure-resistant sealed vessel, were dissolved 1.42 g of 2,6-dichlorobenzoic acid (7.3 mM) and 0.38 g of cuprous chloride (3.8 mM) in 25 ml of an ethanol solution containing 20% dimethylamine (about 20 g) prior to addition of ethanol to a total volume of 50 ml. The reaction system was substituted with an $N_2$ atmosphere, and a manometer was mounted on the vessel prior to sealing, followed by heating at 80° C. After the heating, the pressure inside the system was 0.65-0.75 kgf/cm². The reaction mixture solution was analyzed periodically over time by GC-MS$_{E1}$ in the same manner as in Example 4, in order to follow the progress of the reaction. As a result, 15 hours later, the reaction was completed. Effecting the subsequent process in the same manner as in Example 4, 1.1 g of 2,6-diethoxybenzoic acid was obtained (yield of 71.8%). o-Ethoxybenzoic acid was also obtained as a byproduct (7%).

The physical data of the resulting 2,6-diethoxybenzoic acid was as follows: 60 MHz ¹H-NMR: $\delta^{CDCl3(ppm)}$ 9.0-8.0 (COOH), 7.3 (1H, t), 6.6 (2H, d), 4.1 (4H, q), 1.4 (6H,t), GC-MS$_{E1}$: M/E 210 (M+).

EXAMPLE 6

Synthesis of 2-isobutoxybenzoic acid from o-chlorobenzoic acid

In a pressure-resistant sealed vessel, were dissolved 1.14 g of o-chlorobenzoic acid (7.3 mM) and 0.18 g of cuprous chloride (1.8 mM) in 5 g of an isobutyl alcohol solution containing 20% dimethylamine (about 6.0 ml) prior to addition of isobutyl alcohol to a total volume of 50 ml, followed by heating to 100° C. as in Example 4. The reaction mixture solution was analyzed periodically over time by GC-MS$_{E1}$ in the same manner as in Example 4, in order to follow the progress of the reaction. As a result, 20 hours later, the completion of the reaction was confirmed. Effecting the subsequent process in the same manner as in Example 4, 1.0 g of 2-isobutoxybenzoic acid was obtained (yield of 70.6%). The ester of the above product (3%) and benzoic acid (5%) were also obtained as the byproducts, which were confirmed by ¹H-NMR and GC-MS$_{E1}$.

The physical data of the resulting 2-isobutoxybenzoic acid was as follows:

60 MHz ¹H-NMR: $\delta^{CDCl3(ppm)}$ 10.6-10.1 (COOH), 8.2 (1H, d), 7.6 (1H, t), 7.1 (1H, t), 7.0 (1H, d), 4.0 (2H, d), 2.2 (1H, m), 1.1 (6H, d), GC-MS$_{E1}$: M/E 194 (M+).

The physical data of the ester was as follows:

60 MHz ¹H-NMR: $\delta^{CDCl3(ppm)}$ 7.8 (1H,d), 7.5 (1H, t), 7.0 (1H, t), 6.9 (1H, d), 4.1 (2H, d), 3.8 (2H, d), 2.1 (2H, m), 1.1 (6H, d), 1.0 (6H, d), GC-MS$_{E1}$: M/E 250 (M+).

EXAMPLE 7

Synthesis of 2,6-diisobutoxybenzoic acid from 2,6-dichlorobenzoic acid

In a pressure-resistant sealed vessel, were dissolved 1.42 g of 2,6-dichlorbenzoic acid (7.3 mM) and 0.38 g of copper (I) chloride (3.8 mM) in 20 g of an isobutyl alcohol solution containing 20% dimethylamine (about 25 ml) prior to addition of isobutyl alcohol to a total volume of 50 ml. Effecting reaction at 80° C. in the same manner as in Example 5, the reaction mixture solution was analyzed periodically over time by reversed-phase HPLC and GC-MS$_{E1}$, in order to follow the progress of the reaction. Thirty hours later, the starting materials were absolutely reduced, but almost no change was observed, even after further heating for several hours because of the multiple components. Effecting also the subsequent processes, 1.1 g of 2,6-diisobutoxybenzoic acid (yield of 63.3%) and 0.2 g of 2-chloro-6-isobutoxybenzoic acid (yield of 12.7%) were obtained.

As a byproduct, 2-isobutoxybenzoic acid was obtained (20%).

The physical data of the resulting 2,6-diisobutoxybenzoic acid was as follows:

60 MHz ¹H-NMR: $\delta^{CDCl3(ppm)}$ 10.3-9.8 (COOH), 7.3 (1H, t), 6.6 (2H, d), 3.8 (4H, d), 2.0 (2H, m), 1.0 (12H, d), GC-MS$_{E1}$: M/E 266 (M+).

The physical data of the 2-chloro-6-isobutoxybenzoic acid was as follows:

60 MHz ¹H-NMR: $\delta^{CDCl3(ppm)}$ 10.5-10.0 (COOH), 7.5-6.7 (3H, m), 3.9 (2H, d), 2.1 (1H, m), 1.1 (6H, d), GC-MS$_{E1}$: M/E 228 (M+), 230 (M++2).

In accordance with the present invention, as has been described above, o-alkoxybenzoic acid of a higher purity can be produced at a good yield, following the extremely easy reaction procedure and conditions in atmospheric pressure or under a slight pressure. Thus, the present invention is highly valuable as an industrially applicable process. The o-alkoxybenzoic acid produced by the present invention can be expected to be of use as intermediates for pharmaceutical agents, agricultural chemicals, dyes, fragrance and the like and as a second pharmaceutical solution of dental cement and a component of the adhesive agents for polymers.

What is claimed is:

1. A method for producing o-alkoxybenzoic acid, comprising reacting o-chlorobenzoic acid represented by the following general formula

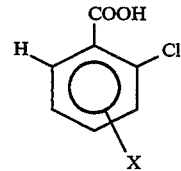

(wherein X is at a meta- or para position and represents hydrogen or halogen) with a lower alcohol in the presence of a copper salt and a lower alkylamine as a catalyst, wherein the reagent ratios of the copper salt, loweralkylamine and lower alcohol per 1 mol of o-dichlorobenzoic acid are in the range of 0.1-0.5 mol, 1-20 mol and 10-150 mol, respectively.

2. A method for producing o-dialkoxybenzoic acid, comprising reacting 2,6-dichlorobenzoic acid represented by the following general formula

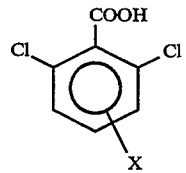

(wherein X represents hydrogen or halogen) with a lower alcohol in the presence of a copper salt and an lower alkylamine as a catalyst.

3. The method for producing o-alkoxybenzoic acid claimed in claim 1 or 2, wherein the lower alkylamine is dimethylamine.

4. The method for producing o-alkoxybenzoic acid claimed in claim 1 or 2, wherein the lower alcohol is an alkyl alcohol with a carbon number of 1 to 5.

5. The method for producing o-alkoxybenzoic acid claimed in claim 1 or 2, wherein the reaction is carried out in an inert-gas (N$_2$) atmosphere under agitation for 1 to 50 hours at 5° to 100° C.

6. The method for producing o-alkoxybenzoic acid claimed in claim 2, wherein the reagent ratios of the copper salt, loweralkylamine and lower alcohol per 1 mol of o-dichlorobenzoic acid are in the range of 0.1–0.5 mol, 1–20 mol and 10–150 mol respectively.

7. The method for producing o-alkoxybenzoic acid claimed in claim 1 or 2 wherein the reagent ratios of the copper salt and loweralkyl amine per 1 mol of o-monochlorobenzoic acid are half the amount used in the case of dichlorobenzoic acid.

8. The method for producing o-alkoxybenzoic acid claimed in claim 1 or 2, wherein the lower alkylamine is monomethylamine.

9. The method for producing o-alkoxybenzoic acid claimed in claim 1 or 2, wherein the copper salt is cuprous chloride, cupric chloride or copper sulfate.

10. The method for producing o-alkoxybenzoic acid claimed in claim 1 or 2, wherein the copper salt is cuprous chloride.

11. The method for producing o-alkoxybenzoic acid claimed in claim 1 or 2, wherein the copper salt is cuprous chloride and the lower alkylamine is monomethylamine.

* * * * *